(12) United States Patent
Li et al.

(10) Patent No.: US 12,416,621 B2
(45) Date of Patent: Sep. 16, 2025

(54) METHOD FOR IDENTIFYING EXUDATIVE SANDSTONE URANIUM DEPOSIT

(71) Applicant: BEIJING RESEARCH INSTITUTE OF URANIUM GEOLOGY, Beijing (CN)

(72) Inventors: Ziying Li, Beijing (CN); Wusheng Liu, Beijing (CN); Mingkuan Qin, Beijing (CN); Yuqi Cai, Beijing (CN); Qingyin Guo, Beijing (CN); Feng He, Beijing (CN); Jun Zhong, Beijing (CN); Xide Li, Beijing (CN); Ye Sun, Beijing (CN); Yunlong Zhang, Beijing (CN); Weitao Li, Beijing (CN); Guo Wang, Beijing (CN); Shengfu Li, Beijing (CN); Jianfang Cai, Beijing (CN); Gui Wang, Beijing (CN); Shan Jiang, Beijing (CN); Jielin Zhang, Beijing (CN); Sheng He, Beijing (CN); Qubo Wu, Beijing (CN); Zilong Zhang, Beijing (CN); Chiheng Liu, Beijing (CN); Linfei Qiu, Beijing (CN); Hu Liu, Beijing (CN); Hongwei Ji, Beijing (CN); Qiang Guo, Beijing (CN); Pengfei Zhu, Beijing (CN); Xinyang Liu, Beijing (CN); Yuyan Zhang, Beijing (CN); Zhixin Huang, Beijing (CN); Jian Guo, Beijing (CN); Meizhi Han, Beijing (CN); Zhongbo He, Beijing (CN); Jinrong Lin, Beijing (CN); Licheng Jia, Beijing (CN); Junxian Wang, Beijing (CN); Longsheng Yi, Beijing (CN); Mingming Tian, Beijing (CN); Xiaoneng Luo, Beijing (CN); Bo Peng, Beijing (CN); Xiaoqian Xiu, Beijing (CN); Ruixiang Hao, Beijing (CN); Wenquan Wang, Beijing (CN); Changfa Yu, Beijing (CN)

(73) Assignee: BEIJING RESEARCH INSTITUTE OF URANIUM GEOLOGY, Beijing (CN)

(*) Notice: Subject to any disclaimer, the term of this patent is extended or adjusted under 35 U.S.C. 154(b) by 0 days.

(21) Appl. No.: 18/356,361

(22) Filed: Jul. 21, 2023

(65) Prior Publication Data
US 2024/0310352 A1    Sep. 19, 2024

(30) Foreign Application Priority Data

Jul. 22, 2022  (CN) .......................... 202210861541.8

(51) Int. Cl.
*G01N 33/24* (2006.01)
*G01V 9/00* (2006.01)
*G01V 11/00* (2006.01)

(52) U.S. Cl.
CPC ............... *G01N 33/24* (2013.01); *G01V 9/00* (2013.01); *G01V 11/00* (2013.01)

(58) Field of Classification Search
CPC ........... G01N 33/24; G01V 9/00; G01V 11/00
See application file for complete search history.

(56) References Cited

FOREIGN PATENT DOCUMENTS

CN         114943311 B   * 10/2022
WO   WO-2023004530 A1   *  2/2023

* cited by examiner

*Primary Examiner* — Krystine E Breier
(74) *Attorney, Agent, or Firm* — Westman, Champlin & Koehler, P.A.

(57) ABSTRACT

The present disclosure relates to a method for analyzing a geological body with the help of physical and chemical properties thereof, and in particular, to a method for identifying an exudative sandstone uranium deposit. With the (Continued)

method for identifying an exudative sandstone uranium deposit according to the embodiments of the present disclosure, an exudative sandstone uranium deposit formed by an exudation metallogenesis may be systematically identified, so as to guide prediction and prospecting evaluation of a uranium deposit in red variegated sandstone formations of a sedimentary basin, avoid ore dislocation and ore leakage, open up new prospecting positions and spaces, and break through new uranium resources.

19 Claims, 7 Drawing Sheets

METHOD FOR IDENTIFYING EXUDATIVE SANDSTONE URANIUM DEPOSIT

CROSS-REFERENCE TO RELATED APPLICATION

This application claims the priority of Chinese Patent Application No. 202210861541.8 filed on Jul. 22, 2022 in the China National Intellectual Property Administration, the content of which is incorporated herein by reference in entirety.

TECHNICAL FIELD

The present disclosure relates to a method for analyzing a geological body with the help of physical and chemical properties thereof, and in particular, to a method for identifying an exudative sandstone uranium deposit.

BACKGROUND

The prediction and prospecting evaluation of a sandstone uranium deposit are usually based on infiltration metallogenesis, and are carried out for an infiltrative sandstone uranium deposit. There is an urgent need for a method that may systematically identify an exudative sandstone uranium deposit to guide prediction and prospecting evaluation of a uranium deposit in red variegated formations in a sedimentary basin.

SUMMARY

In view of the above problem, according to the present disclosure there is provided a method for identifying an exudative sandstone uranium deposit to overcome the above problem or at least partially solve the above problem.

According to the embodiments of the present disclosure, there is provided a method for identifying an exudative sandstone uranium deposit, including: determining a metallogenic depression region in a sedimentary basin, wherein a region in the sedimentary basin where an oxidized color formation is developed and a reduced color formation is developed below the oxidized color formation is determined as the metallogenic depression region; determining a uranium source region in the metallogenic depression region, wherein a region having a uranium content greater than a preset value in the reduced color formation is determined as the uranium source region; determining a region where an exudation fluid is developed in the metallogenic depression region; determining a fluid migration pathway in the metallogenic depression region; determining a metallogenic sand body distribution region in the oxidized color formation; determining a uranium-producing reduced color sand body distribution region formed by an action of the exudation fluid in the metallogenic sand body distribution region; determining an exudation uranium mineralization development location in the metallogenic depression region, wherein the exudation uranium mineralization development location is determined in the metallogenic depression region based on the region where the exudation fluid is developed, the fluid migration pathway, the metallogenic sand body distribution region and the uranium-producing reduced color sand body distribution region; and determining whether a uranium ore body in the exudation uranium mineralization development location is the exudative sandstone uranium deposit, wherein it is determined whether the uranium ore body in the exudation uranium mineralization development location is the exudative sandstone uranium deposit based on at least one of a shape of the uranium ore body, a symbiont of the uranium ore body, a thickness of the reduced color sand body, and an element component of the uranium ore body in the exudation uranium mineralization development location.

With the method for identifying an exudative sandstone uranium deposit according to the embodiments of the present disclosure, an exudative sandstone uranium deposit formed by an exudation mineralization may be systematically identified, so as to guide prediction and prospecting evaluation of a uranium deposit in red variegated sandstone formations of a sedimentary basin.

DETAILED DESCRIPTION OF EMBODIMENTS

Figure 1:
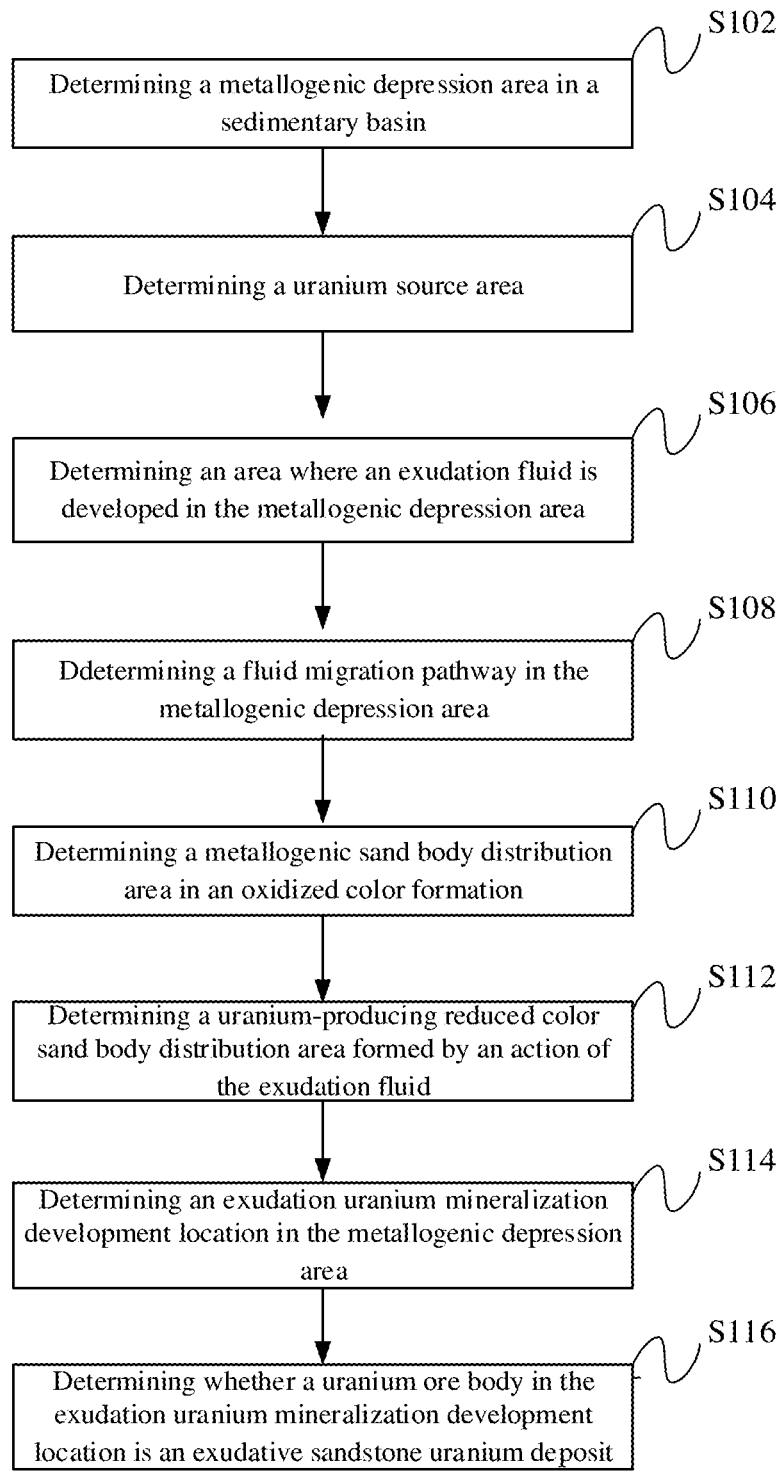
FIG. 1 shows a flowchart of a method for identifying an exudative sandstone uranium deposit according to the embodiments of the present disclosure.

In order to make the objects, technical solutions and advantages of the present disclosure clearer, the technical solutions of the present disclosure will be described clearly and completely below with reference to the accompanying drawings of the embodiments of the present disclosure. Obviously, the described embodiment is one embodiment of the present disclosure, but not all embodiments. Based on the described embodiment of the present disclosure, all other embodiments obtained by those of ordinary skill in the art without creative effort fall within the protection scope of the present disclosure.

It should be noted that, unless otherwise defined, the technical terms or scientific terms used in the present disclosure have the general meanings understood by those with ordinary skills in the art. If descriptions such as "first" and "second" are involved in the whole text, the descriptions such as "first" and "second" are only used to distinguish similar objects, and should not be construed as indicating or implying their relative importance, sequence, etc. or impliedly indicating the quantity of the represented technical feature. It should be understood that the data described by "first", "second", etc. may be interchanged under appropriate circumstances. If "and/or" appears in the whole text, it means that it includes three parallel solutions. Taking "A and/or B" as an example, it includes solution A, solution B, or solution that A and B are satisfied at the same time.

According to the present embodiments, there is provided a method for identifying an exudative sandstone uranium deposit, including:

Step S102: determining a metallogenic depression region in a sedimentary basin, wherein a region in the sedimentary basin where an oxidized color formation is developed and a reduced color formation is developed below the oxidized color formation is determined as the metallogenic depression region;

Step S104: determining a uranium source region in the metallogenic depression region, wherein a region having a uranium content greater than a preset value in the reduced color formation is determined as the uranium source region;

Step S106: determining a region where an exudation fluid is developed in the metallogenic depression region;

Step S108: determining a fluid migration pathway in the metallogenic depression region;

Step S110: determining a metallogenic sand body distribution region in the oxidized color formation;

Step S112: determining a uranium-producing reduced color sand body distribution region formed by an action of the exudation fluid in the metallogenic sand body distribution region;

Step S114: determining an exudation uranium mineralization development location in the metallogenic depression region, wherein the exudation uranium mineralization development location is determined based on the region where the exudation fluid is developed, the fluid migration pathway, the metallogenic sand body distribution region and the uranium-producing reduced color sand body distribution region in the metallogenic depression region; and Step S116: determining whether the uranium ore body in the exudation uranium mineralization development location is an exudative sandstone uranium deposit based on at least one of a shape of the uranium ore body, a symbiont of the uranium ore body, a thickness of the reduced color sand body, and an element component of the uranium ore body in the exudation uranium mineralization development location.

Exudation metallogenesis mainly refers to that a uranium-containing reduced fluid exuded from a deep portion of a metallogenic location migrates into a fully oxidized sand body on an upper portion, and forms a uranium mineralization due to changes in pH, temperature, pressure and redox property etc. Contrary to the typical infiltration water uranium metallogeny theory, in order to be able to systematically determine an exudative sandstone uranium deposit, the present disclosure further improves the exudation metallogenesis theory, and proposes several ore controlling factors in the exudation metallogenesis.

Figure 2:
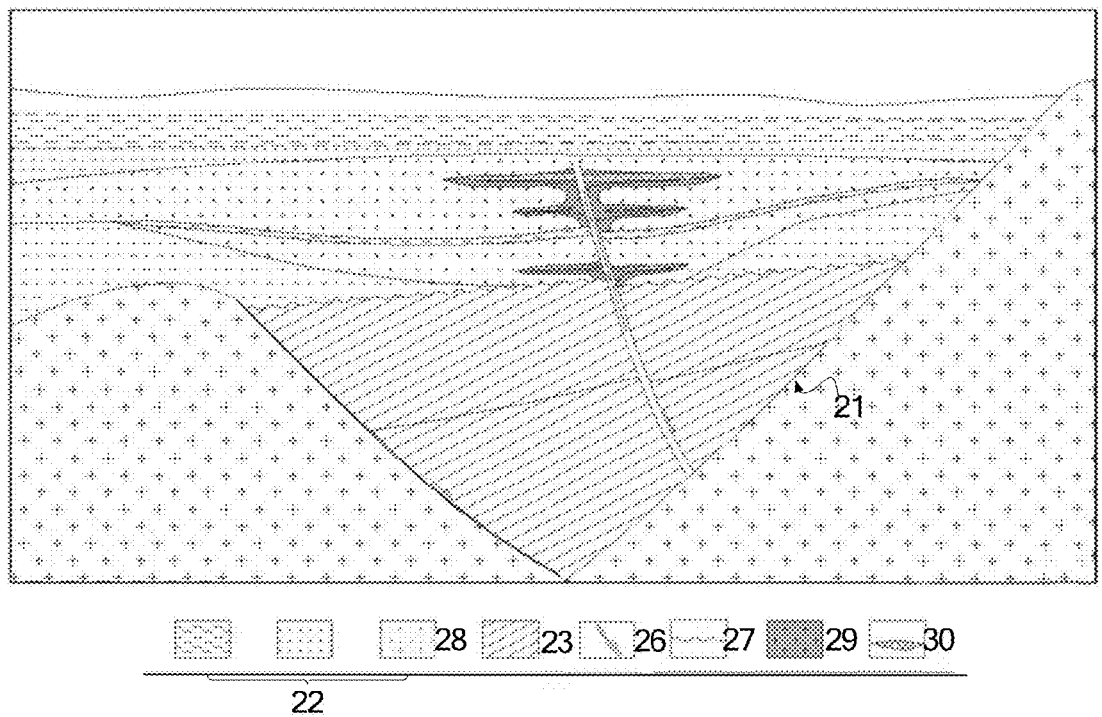
FIG. 2 shows a schematic cross-sectional view of an exudation uranium metallogenesis according to the embodiments of the present disclosure.

FIG. 2 shows a schematic diagram of an exudation metallogenesis. First, it is proposed in the present disclosure that an exudative sandstone uranium deposit mainly exists in an oxidized color formation of a sedimentary basin. An oxidized color usually presents red, brown-red, etc., which is usually called red variegated in the art. Further, a necessary condition for an existence of a reduced fluid required for an exudation metallogenesis is that a reduced color formation is developed below the oxidized color formation. A reduced color usually presents gray, black, etc., and common reduced color formations include a hydrocarbon source rock, a gray mudstone, etc.

Such oxidized color formation and reduced color formation therebelow are usually developed in a depression region of a sedimentary basin. Therefore, in step S102 of the present disclosure, a metallogenic depression region in a sedimentary basin is first determined. A sedimentary basin usually include structural units of three levels, i.e., a basement, a depression, and a cover deposition. A metallogenic depression region refers to a depression where the oxidized color formation and the reduced color formation described above are developed. As such depression is conducive to an exudation uranium metallogenesis, it is called a metallogenic depression region. As an example, referring to FIG. 2, in the metallogenic depression region 21, the oxidized color formation 22 described above is developed, and the reduced color formation 23 is developed below the oxidized color formation 22.

Further, another necessary condition for the exudation metallogenesis is that a uranium source needs to exist in the reduced color formation developed below the oxidized color formation. Therefore, in step S104, a uranium content in the reduced color formation needs to be detected, and a region where the uranium content is greater than a preset value is determined as the uranium source region. Those skilled in the art may use a common detection means to determine the uranium content in the reduced color formation, and the preset value of the uranium content may be determined by those skilled in the art according to the actual situation and relevant standards, which is not limited. As an example, the lithology and the uranium content in the reduced color formation may be determined by performing sampling and analysis as well as drilling core analysis to a leakage profile rock of the reduced color formation, or performing radioactive logging to the reduced color formation, etc. The preset value is set to be $10 \times 10^{-6}$, and a region where a hydrocarbon source rocks or a gray mudstone is developed and the uranium content is greater than $10 \times 10^{-6}$ in the reduced color formation is determined as the uranium source region. As an example, referring to FIG. 2 and FIG. 3, a region of a hydrocarbon source rock, a gray mudstone etc. where the uranium content is greater than the preset value in the reduced color formation 23 in FIG. 2 is determined as the uranium source region 24 in FIG. 3.

Figure 3:
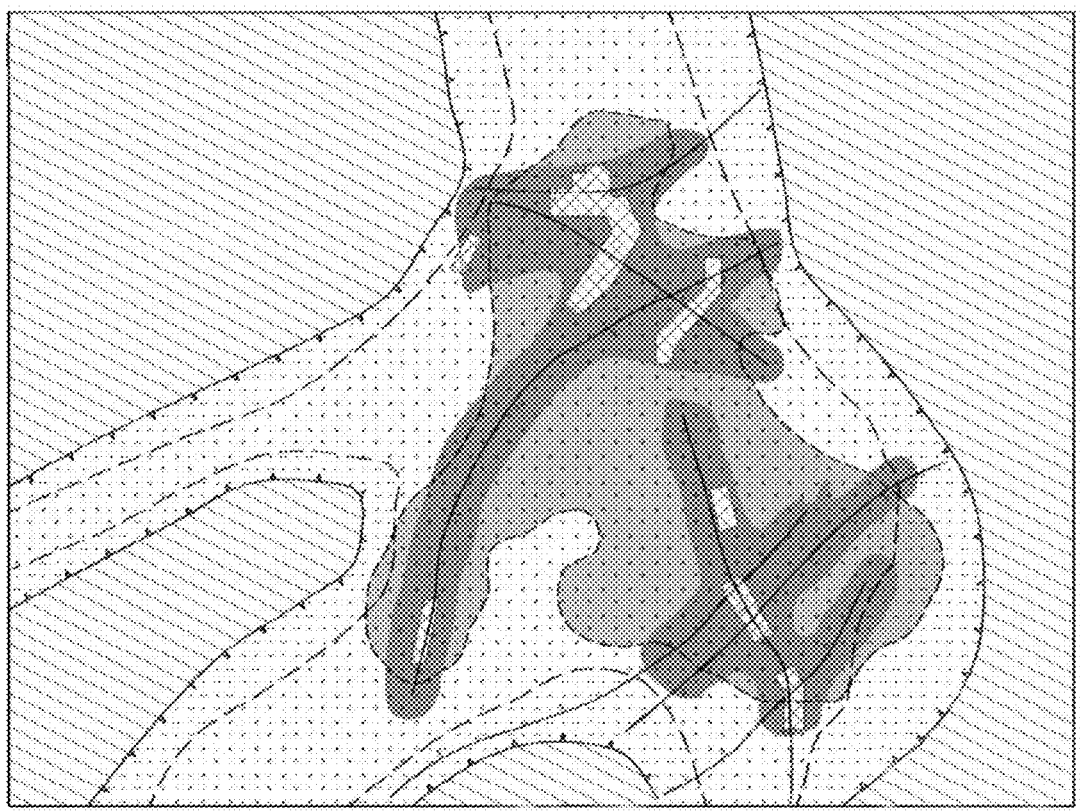
FIG. 3 shows a schematic plan view of an exudation uranium metallogenesis according to the embodiments of the present disclosure.

After the uranium source region is determined, in step S106, it is necessary to determine whether an exudation fluid required for an exudation uranium metallogenesis exists in the uranium source region. As described above, the exudation fluid is a uranium-containing reduced fluid, which is usually rich in organic matters, thiophilic elements, etc. A component analysis may be performed on a fluid inclusion in the reduced color formation or the oxidized color formation. If it is determined that the above matters exist therein, it may be considered that an exudation fluid is developed. Several methods for determining an exudation fluid will be described in detail in the relevant portions of the text below, and will not be repeated here. FIG. 3 shows a region 25 where an exudation fluid is developed in the uranium source region 24.

Further, the exudation fluid in the reduced color formation needs to exude into the oxidized color formation through a migration pathway. Therefore, in step S108, it is necessary to determine the migration pathway of the exudation fluid.

The fluid migration pathway needs to communicate the oxidized color formation on an upper side with the reduced color formation on a lower side. Those skilled in the art may determine the fluid migration pathway by means of borehole analysis, fault interpretation, seismic profile analysis, etc. Several methods for determining a fluid migration pathway will be described in detail in the relevant portions of the text below, and will not be repeated here. The fracture structure 26 shown in FIG. 2 and FIG. 3 and an angular unconformity 27 shown in FIG. 2 are both typical fluid migration pathways. It may be observed intuitively in FIG. 2 that the fracture structure 26 communicates the reduced color formation 23 on a lower side with the oxidized color formation 22 on an upper side with.

As described above, the uranium ore body formed by an exudation action is located in the oxidized color formation, and the uranium ore body itself presents a shape of a reduced color sand body, such as a gray sand body. Therefore, in steps S110 and S112, the reduced color sand body in the oxidized color formation is located and confirmed whether to be formed by an action of the exudation fluid.

Specifically, in step S110, a metallogenic sand body distribution region in the oxidized color formation is determined. A metallogenic sand body distribution region refers to a sand body region that is favorable for sandstone-type uranium metallogenesis. Generally speaking, the sand body distribution region in the reduced color formation with a larger scale and a better connectivity is a sand body region that is favorable for sandstone-type uranium V. Those skilled in the art may determine a sand body distribution region that is favorable for uranium metallogenesis therein by commonly used methods for locating a sand body in the art such as performing a sedimentary system analysis to the oxidized color formation. The method for determining a metallogenic sand body distribution region will be described in detail in the relevant portion of the text below, and will not be repeated here. FIG. 2 and FIG. 3 show the metallogenic sand body distribution region 28 in the reduced color formation 22.

It may be understood that the sand bodies in the metallogenic sand body distribution region usually include an oxidized sand body and a reduced color sand body, wherein the reduced color sand body is a uranium-producing sand body. In step S112, it is necessary to analyze the reduced color sand body in the metallogenic sand body distribution region to determine whether it is a uranium-producing sand body and whether it is a reduced color sand body formed by an action of the exudation fluid. If it is determined to be a uranium-producing sand body and formed by an action of the exudation fluid, it may be delineated as a uranium-producing reduced color sand body distribution region. FIG. 2 shows the uranium-producing reduced color sand body distribution region delineated in the metallogenic sand body distribution region 28.

Those skilled in the art may sample the reduced color sand body, and analyze one or more of its shape, content, uranium content, element enrichment (such as deep source basic elements Co, Ni and sulfophile elements Zn, Mo), and whether a foreign organic matter (for example, a flow dynamic organic matter, such as asphalt and hydrocarbon) brought by the exudation fluid being developed to determine whether it is formed by an action of the exudation fluid. Some methods for determining a reduced color sand body formed by an action of the exudation fluid will be described in detail in the relevant portions of the text below, and will not be repeated here.

Further, after the region where an exudation fluid is developed in the uranium source region, the fluid migration pathway, the metallogenic sand body distribution region, and the uranium-producing reduced color sand body distribution region are determined by the above steps, an exudation uranium mineralization development location may be determined in the metallogenic depression region based on these regions.

As described above, the general principle of exudation uranium metallogenesis is that a reduced fluid exuded from a deep portion of a metallogenic location migrates into a fully oxidized sand body on an upper side and is developed to form uranium mineralization by a redox reaction.

Specifically in the present embodiment, if a fluid migration pathway exists in the region where an exudation fluid is developed in the uranium source region, it means that the exudation fluid may migrate to the oxidized color formation on an upper side through the fluid migration pathway. If a uranium-producing reduced color sand body distribution region formed by an action of the exudation fluid is developed in the oxidized color formation in connection with the fluid migration pathway, it means that the uranium-producing reduced color sand body in this place undergoes a redox reaction by an action of exudation fluid, and a uranium ore body is more likely to be developed in this uranium-producing reduced color sand body distribution region.

That is, a region where the above conditions are satisfied at the same time may be an exudation uranium mineralization development location. Therefore, referring to FIG. 2 and FIG. 3, the region 25 where an exudation fluid is developed, the fluid migration pathway (including regions of the fracture structure 26 and the angular unconformity 27 shown in the figures), the metallogenic sand body distribution region 28, and the uranium-producing reduced color sand body distribution region 29 are superimposed, and a superimposed region of these regions may be determined as an exudation uranium mineralization development location 30.

After the exudation uranium mineralization development location 30 is determined through the above steps, the uranium ore body in these exudation uranium mineralization development locations 30 may be analyzed. It may be finally determined whether the uranium ore body is an exudative sandstone uranium deposit based on a shape of the uranium ore body, a symbiont of the uranium ore body, a thickness of the reduced color sand body, and an element component of the uranium ore body in the exudation uranium mineralization development location.

According to the method for determining an exudative sandstone uranium deposit in the present embodiment, an exudation uranium metallogenesis may be determined systematically. It may be understood that if it is finally determined that the uranium ore body in the exudation uranium mineralization development locations 30 is an exudative sandstone uranium deposit, the distribution range and the uranium content of the uranium ore body in these exudation uranium mineralization development locations may be comprehensively evaluated based on the principle of the exudation uranium metallogenesis, so as to avoid occurrence of ore leakage, ore missing etc.

In some embodiments, the determining a metallogenic depression region in a sedimentary basin in step S102 may specifically include: determining a depression region in the sedimentary basin; and determining a region in the depression region where the oxidized color formation is developed, the reduced color formation is developed below the oxidized color formation, and the reduced color formation having a thickness greater than a second preset value is determined as the metallogenic depression region, wherein the reduced color formation includes a gray mudstone and/or a hydrocarbon source rock.

Specifically, in the process of determining the metallogenic depression region, the depression region in the sedimentary basin may be determined first. Those skilled in the art may collect geology data, geophysical prospecting data, especially seismic data, and drilling data of the sedimentary basin to analyze and divide the basin into three level structural units, i.e. basement, depression, cover deposition, thereby determining the depression in the basin.

After the depression region is determined, the formation composition in the depression region is analyzed to determine the oxidized color formation and the reduced color formation. In the present embodiment, the reduced color formation may specifically include a hydrocarbon source rock and a gray mudstone. As described above, the formation of an exudation uranium metallogenesis requires the development of an exudation fluid in the reduced color formation. The hydrocarbon source rock itself is a rock that may produce or has produced mobile hydrocarbons, in which an exudation fluid is more likely to be developed, while the gray mudstone does not have such property. Therefore, if the reduced color formation is a grey mudstone, its thickness needs to be greater than the second preset value, so that an exudation fluid is more likely to be developed in the determined reduced color formation, thereby improving the determination efficiency. As an example, the second preset value may be 100 m, and those skilled in the art may also select a suitable second preset value as required, which is not limited here.

Compared with a uranium deposit formed by infiltration metallogenesis, an exudative sandstone uranium deposit formed by exudation metallogenesis usually has a larger burial depth, and its theoretical metallogeneic depth may reach more than 2000 m. Therefore, in some embodiments, if a depression region in a sedimentary basin is determined, a region in the sedimentary basin having a depression basement burial depth greater than 1500 m and an area greater than 800 km$^2$ may be determined as a depression region, thereby improving the determination efficiency.

Several methods for determining a region where an exudation fluid is developed will be described below, and the following methods may be used individually or in combination to determine a region where an exudation fluid is developed.

In some embodiments, the determining a region where an exudation fluid is developed in the metallogenic depression region in step S106 may include: determining a composition, a temperature and a salinity of a fluid inclusion in the reduced color formation; an determining that the exudation fluid is developed in the region where the reduced color formation is located if an organic matter is developed in the fluid inclusion, and the temperature is greater than 90° C. and the salinity is greater than 4%.

A fluid inclusion refers to that a fluid trapped during a mineral crystal growth is enclosed in minerals. The composition and properties of the fluid inclusion may be determined by analyzing the composition, temperature and salinity thereof, so as to determine whether it is an exudation fluid in the exudation uranium metallogenesis. Those skilled in the art may sample the reduced color formation, and then prepare a fluid inclusion sheet for analysis to obtain the components therein, and they may use a laser Raman spectrometer, an infrared spectrometer, a gas chromatograph, an isotope mass spectrometer, etc. for component analysis, which is not limited here. Further, the temperature and salinity of the fluid inclusion may be measured using a microscopic cooling and heating table. In the present embodiment, if it is determined that an organic matter is developed in the fluid inclusion, and the fluid temperature is greater than 90° C. and the salinity is greater than 4% NaCl.eq. it may be determined that it is an exudation fluid, and further it may be determined that the exudation fluid is developed in this reduced color formation.

In some embodiments, in addition to determining an exudation fluid by analyzing a fluid inclusion in a reduced color formation, an oxidized color formation may also be analyzed. If traces of an action of an exudation fluid exist in an oxidized color formation, it may also be determined that an exudation fluid is developed in a region near the oxidized color formation.

Specifically, a content of uranium and sulfophile elements in a reduced color sand body may be determined in the oxidized color formation; a content of uranium and sulfophile elements in the oxidized color sand body distributed at a same time and space as the reduced color sand body may be determined; and it is determined that the exudation fluid is developed in the region where the reduced color sand body is located if the content of uranium and sulfophile elements in the reduced color sand body is greater than the content of uranium and sulfophile elements in the oxidized color sand body and exceeds a third preset value.

It is understood that if a reduced color sand body exists in an oxidized color formation, the reduced color sand body must have undergone a redox reaction, and if the redox reaction is formed by an action of an exudation fluid, it will make the reduced color sand body there to have a higher uranium and sulphophile elements content compared with the oxidized color sand body. Therefore, the content of uranium and sulfophile elements in the reduced color sand body may be compared with the content of uranium and sulfophile elements in the oxidized color sand body distributed at a same time and space as the reduced color sand body to determine whether an exudation fluid is developed. In the present embodiment, the third preset value may be determined by those skilled in the art as required. As an example, the third preset value may be 30%.

Several methods for determining a fluid migration pathway will be described next, and these methods may be used individually or in combination to determine a fluid migration pathway.

In some embodiments, the determining a fluid migration pathway in the metallogenic depression region specifically includes: determining a fracture structure in the metallogenic depression region connecting the reduced color formation with the oxidized color formation as the fluid migration pathway.

Specifically, those skilled in the art may select to perform a horizon and fault interpretation to the boreholes and seismic profile in the metallogenic depression region to determine the fracture structure therein, and then determine the fracture structure connecting the reduced color formation with the oxidized color formation as the fluid migration pathway.

In some embodiments, the determining a fluid migration pathway in the metallogenic depression region may include: determining a region where a riverway is developed in the oxidized color formation and a region where the riverway is cut down to the reduced color formation as the fluid migration pathway.

Specifically, those skilled in the art may also determine a region where a riverway is developed in the oxidized color formation by a geological profile analysis, and further judge whether the riverway region is cut down to the reduced color formation. If it is cut down to the reduced color formation, it means that it communicates the oxidized color formation with the reduced color formation, and may be determined as the fluid migration pathway.

In some embodiments, the determining a fluid migration pathway in the metallogenic depression region may include: determining a region exhibiting an unconformity of a contact relationship between the oxidized color formation and the reduced color formation as the fluid migration pathway.

Specifically, those skilled in the art may analyze the contact relationship between the reduced color formation and the oxidized color formation. If the contact relationship exhibits an angular unconformity, it may be determined that this is a fluid migration pathway. An angular unconformity means that after the formation of the underlying strata, due to folds, fractures, bending, magma intrusion, etc. caused by a crustal movement, the crust rises and suffers weathering and denudation, when the crust sinks again to receive sedimentation, a new overlying stratum is formed, the attitudes of the overlying new stratum and the underlying old stratum are completely different, and obvious stratum loss and weathering and denudation exist therebetween.

In some embodiments, the angle of unconformity between the reduced color formation and the oxidized color formation needs to be large enough to ensure that a fluid migration pathway may be formed there.

In some embodiments, the determining the fluid migration pathway in the metallogenic depression region may specifically include: determining a region lifted to the surface of the earth due to tilting in the reduced color formation as the fluid migration pathway.

Specifically, a fold structure analysis may be performed to the metallogenic depression region, and a region in the reduced color formation lifted to the surface of the earth due to tilting, i.e., the structure skylight region described in the art, is determined as the fluid migration pathway.

In some embodiments, the determining a metallogenic sand body distribution region in the oxidized color formation may specifically includes: determining a fluvial facies region in the oxidized color formation; and determining a region in the fluvial facies region where a sand body thickness is greater than 20 m and an area is greater than 30 km$^2$ as the metallogenic sand body distribution region.

As described above, the metallogenic sand body distribution region is a region having a large-scale sand body distribution and a good connectivity. According to the general principle of sand body formation, it is usually developed in a fluvial facies region. Therefore, a fluvial facies region in the oxidized color formation is first determined, and then a region in the fluvial facies region where a sand body thickness is greater than 20 m and an area is greater than 30 km$^2$ is determined as the metallogenic sand body distribution region. Those skilled in the art may also use other suitable methods to locate a sand body in the oxidized color formation and determine the metallogenic sand body distribution region, which is not limited here.

In some embodiments, the determining a uranium-producing reduced color sand body distribution region formed by an action of the exudation fluid in the metallogenic sand body distribution region may include: sampling and analyzing the reduced color sand body in the metallogenic sand body distribution region to determine whether the reduced color sand body is formed by an action of the exudation fluid and whether it is a uranium-producing reduced color sand body.

As described above, a condition that a uranium-producing reduced color sand body needs to satisfy is that the reduced color sand body therein is a uranium-producing sand body and is formed by an action of the exudation fluid. Therefore, the reduced color sand body may be sampled and analyzed to determine whether it is a uranium-producing sand body and is formed by an action of the exudation fluid.

In some embodiments, it may be determined whether the reduced color sand body is a uranium-producing sand body by analyzing a uranium content in the reduced color sand body. The reduced color sand body is determined as the uranium-producing reduced color sand body if the uranium content in the reduced color sand body is greater than a fifth preset value. Those skilled in the art may determine the fifth preset value according to relevant technical standards. As an example, the fifth preset value may be $10 \times 10^{-6}$.

Several methods that may determine whether a reduced color sand body is formed by an action of the exudation fluid will be described below, and the following methods may be used individually or in combination to determine whether a reduced color sand body is formed by an action of the exudation fluid.

In some embodiments, the reduced color sand body may be sampled, and sandstone rock mineral characteristics of the reduced color sand body may be analyzed. It may be determined that the reduced color sand body is formed by an action of the exudation fluid if the sandstone rock mineral characteristics in the reduced color sand body include at least one of the following: a limonitization spot existing in the reduced color sand body, a limonitization spot existing in a boulder clay enclosed by the reduced color sand body, and the reduced color sand body being embedded in the oxidized color sand body along a fracture.

In some embodiments, the reduced color sand body may be sampled, and an element enrichment in the reduced color sand body may be analyzed. It may be determined that the reduced color sand body is formed by an action of the exudation fluid if an enrichment of deep source basic elements Co, Ni and sulfophilic elements Zn, Mo in the reduced color sand body is higher than that of a primary sand body and exceeds a fourth preset value. A primary sand body may be defined as a sand body that is not affected by the exudation fluid.

Those skilled in the art may sample and analyze the primary sand body around the reduced color sand body to determine the element content in the primary sand body, and compare it with that in the reduced color sand body, or a general value of the element content in the sand body in the art may also be used for comparison with the element content in the reduced color sand body, which is not limited here. Those skilled in the art may set the fourth preset value as required. As an example, for a uranium mineralization sample, the fourth preset value may be 2 times.

In some embodiments, the reduced color sand body may be sampled, and a source of the organic matter in the reduced color sand body may be analyzed. It is determined that the reduced color sand body is formed by an action of the exudation fluid if an organic matter originating from the reduced color formation exists in the reduced color sand body.

The organic matter here may include, but is not limited to, coal seams, coal lines, plant debris and remains, carbon debris, microorganisms, (ground) asphalt, various organic acids, humic substances, and dispersed free or adsorbed hydrocarbons, oil and gas and other organic substances. If an organic matter originating from the reduced color formation exists in the reduced color sand body, the organic matter is more likely to be brought by the exudation fluid, and it may be determined that the reduced color sand body is formed by an action of the exudation fluid.

In some embodiments, the source of the organic matter may be identified based on the type of organic matter in the reduced color sand body. First, the type of organic matter in the reduced color sand body is determined. If it is determined that the type of organic matter in the reduced color sand body includes at least one of hydrocarbon, asphalt and sapropelic kerogen, it may be determined that an organic matter originating from the reduced color formation exists in the reduced color sand body, and it is further determined that the reduced color sand body is formed by an action of the exudation fluid.

Hydrocarbon organic matter may include gaseous hydrocarbon and liquid hydrocarbon. It is proposed in the present disclosure that the hydrocarbons in the reduced color sand body usually originate from the reduced color formation below the oxidized color formation, such as hydrocarbon source rocks developed below the oxidized color formation. Therefore, it may be used as evidence for an existence of an organic matter originating from the reduced color formation in the reduced color sand body that the types of organic matter in the reduced color sand body include hydrocarbons.

Ground asphalt is also called asphalt in the art. It is proposed in the present disclosure that the solid organic matter in the organic matter originating from the reduced color formation usually occurs in the interstitial material of the reduced color sand body in the form of ground asphalt. Therefore, it may be used as evidence for an existence of an organic matter originating from the reduced color formation in the reduced color sand body that the types of organic matter in the reduced color sand body include ground asphalt.

Kerogen refers to the dispersed organic matter in a sedimentary rock that is insoluble in alkalis, non-oxidizing acids and non-polar organic solvents. The properties of kerogen formed from different sources of organic matter are quite different. Kerogen mainly includes three types. Type I kerogen also known as sapropel kerogen: it mainly contains lipid compounds, many strait-chain alkanes, few polycyclic aromatic hydrocarbons and oxygen-containing functional groups, and has high hydrogen content and low oxygen content. Type II kerogen: the hydrogen content is higher, but slightly lower than that of type I kerogen, it is a highly saturated polycyclic carbon skeleton, contains more medium-length straight-chain alkanes and cycloalkanes as well as polycyclic aromatic hydrocarbons and heteroatom functional groups. Type III kerogen also known as humic kerogen: it has a low hydrogen content and a high oxygen content, mainly contains polycyclic aromatic hydrocarbons and oxygen-containing functional groups, has few saturated hydrocarbons, and it is derived from terrestrial higher plants.

It is proposed in the present disclosure that the organic matter originating from the reduced color formation usually forms sapropel kerogen, while the organic matter of syngenetic sedimentation usually forms humic kerogen. Therefore, it may be used as evidence for an existence of an organic matter originating from the reduced color formation in the reduced color sand body sample that the types of organic matter in the reduced color sand body sample include sapropel kerogen.

The existence of the above types of organic matter may be used as evidence for an existence of an organic matter originating from the reduced color formation in the reduced color sand body. Therefore, if it is determined that the types of organic matter in the reduced color sand body include any one of the above types, it may be determined that an organic matter originating from the reduced color formation exists in the grey sand body, and it is further determined that formation of the reduced color sand body is related to an action of the exudation fluid.

Further, the above types of organic matter may exist in the reduced color sand body at the same time, and it may be understood that the above types of organic matter present various phases such as gas, liquid and solid. If the above types of organic matter are found in the reduced color sand body at the same time, the possibility of misjudgment will be greatly reduced. Therefore, those skilled in the art may also select to determine that an organic matter originating from the reduced color formation exists in the reduced color sand body only when multiple types of the above types of organic matter are found at the same time, so as to improve the accuracy and reliability of organic matter source identification.

In order to improve the identification efficiency, in some embodiments, identification may be performed only for the types of organic matter mentioned above. In some other embodiments, the organic matter may also be identified more comprehensively and not limited to the above several types of organic matter. If in addition to the above several types of organic matter, other types of organic matter are also identified, and the other types of organic matter indicate other sources of organic matter, further comprehensive analysis may be required to improve the accuracy of the identification results and avoid misjudgment.

Several specific methods for determining the type of organic matter in the reduced color sand body will be described below. Each of the following methods may determine at least one type of organic matter. Those skilled in the art may use the various methods described below individually or in combination as required.

In some embodiments, the determining the type of organic matter in the reduced color sand body may include: observing a morphology of the organic matter debris in the reduced color sand body under a microscope; performing a laser Raman analysis to the observed organic matter debris; and determining that the types of organic matter in the reduced color sand body includes ground asphalt if the organic matter debris presents a vein shaped, no plant cellular structure is seen in the organic matter debris, and double peaks appear in the result of the laser Raman analysis.

Specifically, the collected reduced color sand bodies may be first prepared into polished thin sections, and the specific method for preparing polished thin sections may be completed by those skilled in the art according to relevant test standards, which is not limited. Then, the morphology of organic matter debris in the reduced color sand body may be observed by a polarization microscope. Organic matter debris refers to an organic matter in the shape of debris. In the process of observing the morphology of organic matter debris, it is necessary to pay attention to whether the organic matter debris presents a vein shape, whether it has a flow structure and whether it has a plant cellular structure.

Further, a laser Raman spectroscopic analysis may be performed to the observed organic matter debris, for example. For example, the organic matter debris which presents a vein shape and where no plant cell is seen may be located, and then the laser Raman analysis may be performed to it. If the characteristic peaks in the laser Raman analysis result of the organic matter debris are double peaks, it indicates that the organic matter debris is asphalt, and then it may be further determined that the types of organic matter in the reduced color sand body include ground asphalt.

In addition to the above methods, those skilled in the art may also select other methods commonly used in the art to identify the ground asphalt in the reduced color sand body.

In some embodiments, the determining a type of organic matter in the reduced color sand body may further include: observing the reduced color sand body under a fluorescence microscope, and determining that the types of organic matter in reduced color sand bodies include hydrocarbons if blue and/or yellow fluorescence appears in the reduced color sand body.

Specifically, the reduced color sand body may be first ground into inclusion sheets. In the process of the mineral growth, substances of a gas phase and a liquid phase brought by the metallogenic fluid will exist in the form of an inclusion. Therefore, in the present embodiment, the reduced color sand body is ground into inclusion sheets, and then the inclusions therein are observed with a fluorescence microscope, so as to determine whether it contains hydrocarbons. Similarly, those skilled in the art may grind the inclusion sheets according to relevant test standards. As an example, a thickness of the inclusion sheet may be about 70-80 μm, and a 502 glue may be injected.

Liquid hydrocarbons in the inclusion sheets may mainly be observed under the fluorescence microscope. Under the fluorescence microscope, the liquid hydrocarbons will emit blue or yellow fluorescence. Therefore, if blue and/or yellow fluorescence is observed, it may be determined that the types of organic matter in the reduced color sand body include hydrocarbons.

It is also proposed in the present disclosure that a hydrocarbon-containing inclusion is usually developed in structures such as carbonate cements, quartz enlarged edges, secondary fractures, etc. For this reason, in some embodiments, the reduced color sand body including the above structures may be selected to grind inclusion sheets, and the inclusions developed in the above structures are mainly observed to improve the efficiency.

In some embodiments, the determining a type of organic matter in the reduced color sand body may further include: performing an acidolysis hydrocarbon analysis to the reduced color sand body to determine that the types of organic matter in the reduced color sand body include hydrocarbons.

An acidolysis hydrocarbon analysis is a method commonly used in the art to analyze hydrocarbon substances in sediments, and it may release gaseous hydrocarbon substances and test the hydrocarbon gas component content. As an example, in an acidolysis hydrocarbon analysis, hydrochloric acid may be used to decompose carbonate minerals in the reduced color sand body to release gaseous substances, then an alkaline solution may be used to remove the carbon dioxide gas in the gaseous substances, and last the collected gaseous substances are tested for the hydrocarbon gas component content to determine whether gaseous hydrocarbon substances exist therein.

In some embodiments, the determining a type of organic matter in the reduced color sand body may further include: performing a rock pyrolysis analysis to the reduced color sand body to determine that the types of organic matter in the reduced color sand body include sapropelic kerogen.

There are a plurality of methods for determining a type of kerogen in the art, such as determination based on microscopic features, determination based on an elemental composition, and determination based on biological sources. In the present embodiment, the method of a rock pyrolysis is used to determine a type of kerogen, so as to further determine that the types of organic matter in the reduced color sand body include sapropelic keroge. The sapropelic keroge here generally refers to the Type I kerogen described above. In some embodiments, the sapropelic keroge here may also include humic sapropelic (Type $II_1$) kerogen.

A rock pyrolysis may be completed with reference to relevant standards in the field. As an example, in the process of a rock pyrolysis, the detection conditions may be set as follows: a high purity helium pressure: 0.20-0.30 Mpa, an air pressure: 0.30-0.40 Mpa, and a hydrogen pressure: 0.20-0.30 Mpa. The rock pyrolysis may include but not limited to a number of data such as total organic carbon (TOC), hydrogen index ($I_H$) and oxygen index ($I_O$). Those skilled in the art may analyze the data obtained from a rock pyrolysis according to relevant standards, so as to determine what type of kerogen the kerogen in the reduced color sand body is.

In some other embodiments, those skilled in the art may also use other suitable methods to determine a type of kerogen, for example, by means of a microscope, a fluorescence microscope, a scanning electron microscope, etc. to determine the microscopic composition of the kerogen, and further determine the type thereof. For another example, an infrared spectroscopy is used to determine the functional group composition of the kerogen, and further determine the type thereof.

Further, it is also proposed in the present disclosure that in addition to determining the source of kerogen based on the type of kerogen, the source of kerogen may also be determined based on a maturity of the kerogen, so as to improve the accuracy. Specifically, if the types of organic matter include sapropelic keroge, and the maturity of the sapropelic keroge is higher than a preset value, it is determined that an organic matter originating from the reduced color formation exists in the reduced color sand body.

In the art, the maturity of kerogen is generally divided from low degree to high degree to be immature, mature, highly mature, over mature, etc. As an example, if the maturity of sapropelic keroge is mature and above, it is determined that an organic matter originating from the reduced color formation exists in the reduced color sand body. Those skilled in the art may reasonably set the preset value of maturity according to the actual situation and the method for determining the maturity of kerogen actually used.

In some embodiments, the maturity of kerogen may be determined based on the result of rock pyrolysis, thereby improving the efficiency and reducing the costs without a need for additional tests. In some other embodiments, those skilled in the art may also determine the maturity of kerogen by other suitable method, for example, determination of carbon isotopic composition, functional group composition, microscopic composition, thermal weight loss, vitrinite reflectance etc.

It is also proposed in the present disclosure that in addition to identifying the source of organic matter based on the above types of organic matter, the source of organic matter may also be further identified based on the composition of organic matter. The exudation fluid developed in the reduced color formation usually contains low-level aquatic organisms, such as algae, and the normal alkanes from these low-level aquatic organisms are usually characterized by main peaks with low carbon number.

To this end, in some embodiments, a gas chromatography may be further used to determine the normal alkane carbon number of the soluble organic matter in the reduced color sand body. If the types of organic matter in the reduced color sand body include at least one of hydrocarbon, ground asphalt, and sapropelic keroge, and the normal alkane carbon number of the soluble organic matter is distributed between $C_{15}$ and $C_{22}$, then it is determined that an organic matter originating from the reduced color formation exists in the reduced color sand body.

A soluble organic matter refers to an organic matter in the rock that may be dissolved in an organic solvent, such as the ground asphalt mentioned above. A soluble organic matter may be extracted from a reduced color sand body using organic solvents such as chloroform, dichloromethane, benzene, methanol, and acetone, and then a gas chromatography analysis is performed to the saturated hydrocarbons therein to determine the carbon number of the normal alkanes. If the main carbon peak is between $C_{15}$ and $C_{22}$ in the result of the gas chromatography analysis of the saturated hydrocarbons, it indicates that the saturated hydrocarbons in the soluble organic matter come from lower aquatic organisms, and this may further indicate that an organic matter originating from the reduced color formation exists in the reduced color sand body.

In some embodiments, the pyrite coexisting with the uranium ore body in the reduced color sand body distribution region may be used to determine whether the region is undergone an action of the exudation fluid, and then it is determined whether the reduced color sand body is undergone an action of the exudation fluid. The pyrite-containing sample may be collected in the reduced color sand body distribution region, the location of the zonal structure in the pyrite-containing sample is then determined, and it is determined whether the reduced color sand body is undergone an action of the exudation fluid based on a change in a sulfur isotope value and/or a change in a microelement value in the zonal structure.

Specifically, when it is determined whether the reduced color sand body is undergone an action of the exudation fluid based on a change in a sulfur isotope value, if the sulfur isotope value in the zonal structure gradually decreases from a core of the zonal structure to an edge thereof, it is determined that the reduced color sand body is undergone an action of the exudation fluid.

When it is determined whether the reduced color sand body is undergone an action of the exudation fluid based on a change in a microelement value, the microelements may include arsenic, antimony, cobalt and nickel. If the element contents of arsenic, antimony and a ratio of an element content of cobalt to that of nickel increase gradually from the core of the zonal structure to the edge thereof, it may be determined that the reduced color sand body is undergone an action of the exudation fluid.

A pyrite-containing sample refers to a reduced color sand body containing pyrite, and those skilled in the art may collect the sample based on relevant experience. Preferably, in the process of collecting pyrite-containing sample, pyrite-containing samples with typical attitude are collected as much as possible to facilitate subsequent testing.

After the collection of a pyrite-containing sample is completed, it is necessary to determine the position of the zonal structure of the pyrite in the collected pyrite-containing sample. The distribution and attitude of pyrite in the collected pyrite-containing sample may be characterized by images. For example, the pyrite-containing sample may be ground into polished thin sections, resin targets, fluid inclusion sheets, etc., and then the attitude and distribution of pyrite in the pyrite-containing sample may be determined by microscope observation, energy spectrum scanning images, backscatter electron images, etc., thereby determining the position of the zonal structure of pyrite. The above operations may be completed by analytical instruments commonly used in the art, such as automatic mineral scanners, which is not limited here. It should be noted that the above work process involves the grinding to the collected pyrite-containing sample. In the grinding process, it is necessary to observe the outcrop and the polishing situation of pyrite to ensure the qualities of the ground polished thin section, the fluid inclusion sheet, the resin target, etc.

The zonal structure of pyrite is usually formed by an action of a metallogenic fluid, and in the pyrite-containing sample collected in the reduced color sand body distribution region, the zonal structure of pyrite generally has a similar cause of formation to a uranium ore body in the reduced color sand body, i.e., they are formed by an action of the same metallogenic fluid. For this purpose, a subsequent elemental analysis is performed to the zonal structure of pyrite in the present embodiment.

Figure 4:
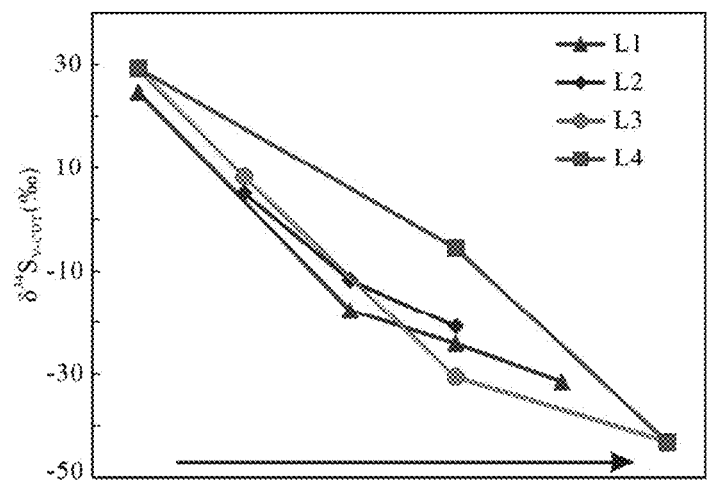
FIG. 4 shows a schematic diagram of a change in a sulfur isotope value from a core portion to an edge portion of a zonal structure according to the embodiments of the present disclosure.

As described above, in some embodiments, a change in a sulfur isotope value in the zonal structure is used to determine that the reduced color sand body is undergone an action of the exudation fluid. FIG. 4 shows a schematic diagram of a change in a sulfur isotope value in a zonal structure of pyrite. Four sets of tests are carried out to form four sulfur isotope value curves of L1, L2, L3 and L4. The left side is the sulfur isotope value near the core of the zonal structure, and the right side is the sulfur isotope value near the edge of the zonal structure. It is proposed in the present disclosure that the exudation fluid is a reduced fluid rich in organic matter, and the organic matter fluid has broad $\delta^{34}S$ characteristics. The zonal structure of pyrite formed by an action of the exudation fluid will present a change trend in FIG. 4, i.e., a gradual downward trend from the core of the zonal structure to the edge thereof. Therefore, if it is determined in step S106 that the sulfur isotope value in the zonal structure gradually decreases from the core of the zonal structure to the edge thereof, it may be determined that the pyrite is undergone an action of the exudation fluid, and then it may be determined that the reduced color sand body is also undergone an action of the exudation fluid.

In some cases, a bacterial sulfate reduction may also lead to a gradual decrease in a sulfur isotope value from the core of the zonal structure to the edge thereof. However, it is proposed in the present disclosure that in the zonal structure of pyrite that is undergone an action of the exudation fluid, there is a large difference in the sulfur isotope values between the core and the edge, and this is impossible to be explained by a bacterial sulfate reduction. Therefore, in some embodiments, in order to improve the judgment accuracy and reduce misjudgment, a further judgment may be made based on a range between the sulfur isotope value of the core of the zonal structure and the sulfur isotope value of the edge thereof. If the sulfur isotope value from the core of the zonal structure to the edge thereof presents a downward trend, and the range of the sulfur isotope value in the zonal structure is greater than a preset value, it is determined that the reduced color sand body is undergone an action of the exudation fluid. It should be noted that a range of a sulfur isotope value here usually refers to a difference between a sulfur isotope value obtained in a specific analysis at one or more positions relatively closest to the core and a sulfur isotope value at one or more positions relatively closest to the edge.

Those skilled in the art may determine the preset value as required. For example, the preset value may be determined by using a general value of a sulfur isotope in the zonal structure of pyrite of other formation causes. In some specific embodiments, the preset value may be set to 60‰.

Figure 5:
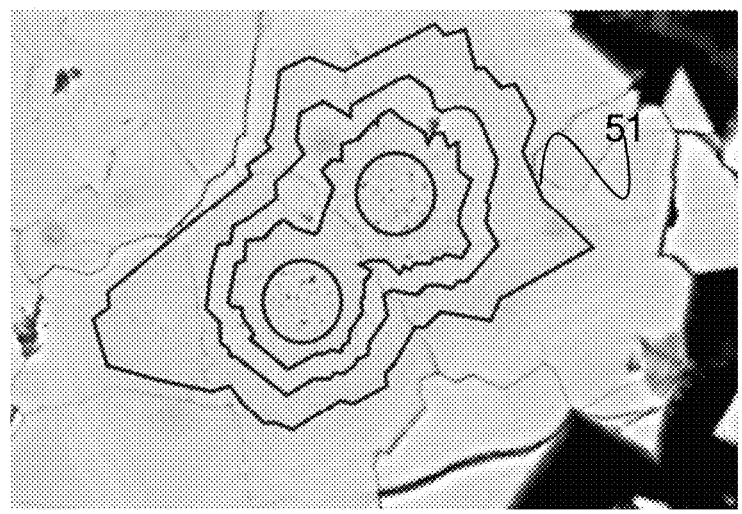
FIG. 5 shows a schematic diagram of a zonal structure according to the embodiments of the present disclosure.

In some embodiments, after the location of the zonal structure of pyrite in the pyrite-containing sample is determined, a plurality of point locations in the zonal structure may be further marked. FIG. 5 shows a schematic diagram of a zonal structure in a pyrite sample. A portion circled by a black strip is the zonal structure 51, wherein the relatively central position is the core of the zonal structure, and the relatively marginal position is the edge of the zonal structure.

Figure 6:
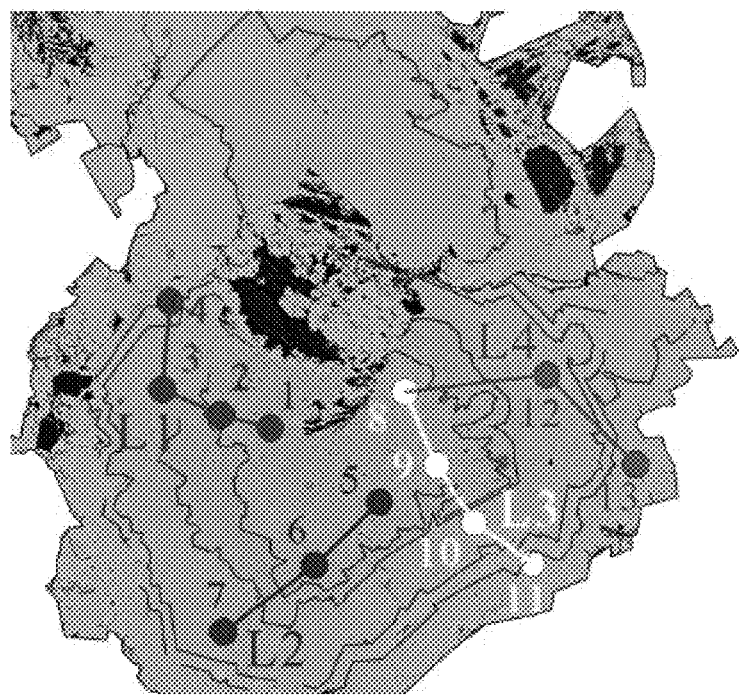
FIG. 6 is a schematic diagram of a distribution of a plurality of point locations according to the embodiment of the present disclosure.

Referring to FIG. 4 together with FIG. 6, FIG. 6 shows a plurality of marked point locations. These point locations are distributed from the core of the zonal structure to the edge thereof, and correspond to the respective data points in the four curves of L1, L2, L3 and L4 in FIG. 4. Those skilled in the art may use appropriate marking methods to mark the point locations, and then an in situ sulfur isotope testing may be performed according to the marked point locations.

The advantage of an in situ sulfur isotope testing is that the sample processing is simpler and more efficient. Specifically, an in-situ sulfur isotope testing may be performed using laser ablation plasma mass spectrometry. In the testing process, those skilled in the art may select an appropriate analysis beam spot and testing time according to the relevant testing requirements and the specific conditions of the sample to obtain data of sulfur isotope values with high efficiency and high accuracy.

In some embodiments, the marked point locations may be divided into multiple groups, and the point locations of different groups may be distributed from the core to the edge in different zonal structures, or may be distributed in different directions of the same zonal structure (for example, one group is from the core to the edge of one side, and another group is from the core to the edge of the other side). Still referring to FIG. 6, point locations 1-4 are group L1, point locations 5-7 are group L2, point locations 8-11 are group L3, and point locations 8 and 12-13 are group L4. In this way, four sulfur isotope value change curves such as L1-L4 shown in FIG. 4 may be obtained, which improves the judgment accuracy, and avoids misjudgment caused by judgment based on only one curve.

Figure 7A:
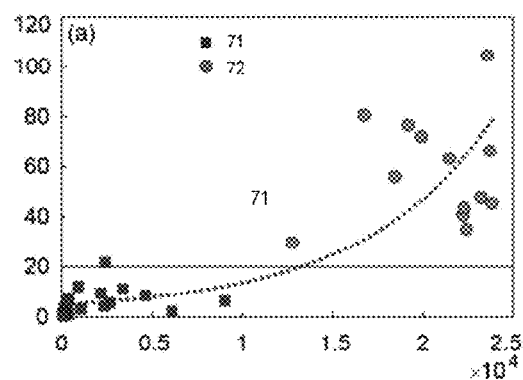
FIG. 7A and FIG. 7B show schematic diagrams of a change in a microelement value in the zonal structure according to the embodiments of the present disclosure.
Figure 7B:
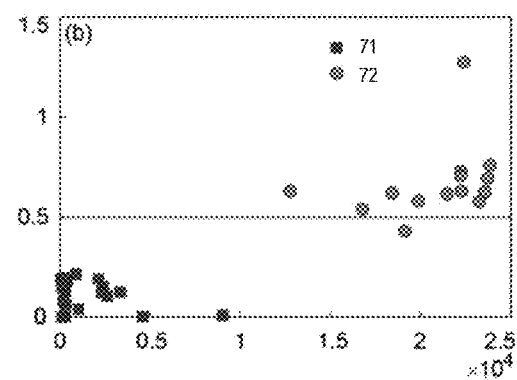

In some embodiments, as described above, it is determined that the reduced color sand body is undergone an action of the exudation fluid based on a change in a microelement value in the zonal structure. FIG. 7A and FIG. 7B show schematic diagrams of a change in a microelement value in an embodiment. The square point indicated by reference sign 71 is the microelement data near the core, and the circle point indicated by reference sign 72 is the microelement data near the edge. In FIG. 7A, the horizontal axis is the arsenic element content, the vertical axis is the antimony element content, and in FIG. 7B, the horizontal axis is the arsenic element content, and the vertical axis is the element content ratio of cobalt/nickel. It may be seen from FIG. 7A that the content of arsenic and antimony elements gradually increases from the core to the edge. It may be seen from FIG. 7B that the element content ratio of cobalt/nickel gradually increases from the core to the edge, which presents a positive synergistic change relationship with the arsenic element content. Therefore, it may be determined that the reduced color sand body is undergone an action of the exudation fluid.

It is also proposed in the present disclosure that, compared with pyrites of other formation causes, in a pyrite formed by an action of the exudation fluid, in addition to a different change trend of the microelements from the core to the edge, the content of the microelements is also relatively high. Therefore, in some embodiments, the arsenic element content, the antimony element content, and the element content ratio of cobalt/nickel may be further compared with the above values in pyrites of other formation causes, for example, with the above values in pyrites formed due to atmospheric precipitation. If they are significantly higher than the above values in the pyrites of other formation causes, it is determined that the reduced color sand body is undergone an action of the exudation fluid, thereby reducing the probability of misjudgment.

The marked multiple point locations may be distributed from the core of the zonal structure to the edge thereof, and an in-situ ion mass spectrometry may be performed at multiple point locations to determine the microelement values at multiple point locations and improve the test efficiency.

The advantage of an in-situ testing is that sample processing is simpler and more efficient. Specifically, an in-situ testing of microelement values may be performed using laser ablation plasma mass spectrometry. In the testing process, those skilled in the art may select an appropriate analysis beam spot and testing time according to the relevant testing requirements and the specific conditions of the sample to obtain data of microelement values with high efficiency and high accuracy.

In some embodiments, when multiple point locations in the zonal structure are marked, in addition to determining the zonal structure and performing marking based on energy spectrum scanning images, backscatter electron images, etc. described above, electron probes may also be used. Specifically, an electron probe may be used to perform an element surface scan to the pyrite in the pyrite-containing sample. In the element plane scan result, the higher the element content is, the stronger the fluorescence is. Thereby, the zonal structure may be observed more clearly, and the distribution and content change trend of some microelements may be observed preliminarily. Therefore, multiple point locations may be marked based on the microelement distribution observed by the element surface scan, so as to avoid marking a point location without a test value.

Figure 8A:
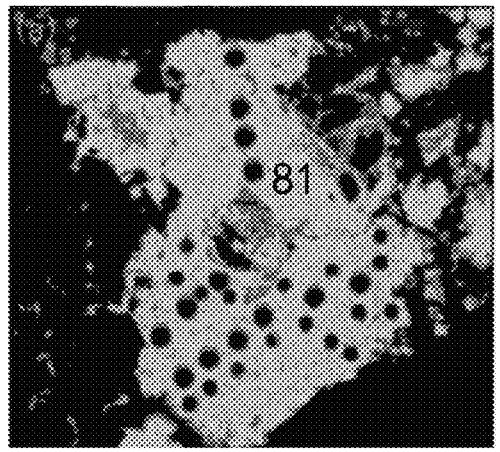
FIG. 8A and FIG. 8B show schematic diagrams of an element surface smayning result according to the embodiments of the present disclosure.
Figure 8B:
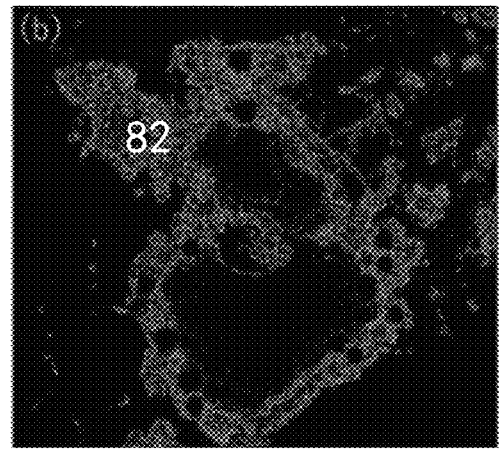

FIG. 8A and FIG. 8B show schematic diagrams of an element surface scan result for an iron element and an arsenic element. The fluorescence in FIG. 8A indicates iron element 81, which outlines a range of a pyrite distribution, and the fluorescence in FIG. 8B indicates an arsenic element 82. It may be seen from the figure that the content of arsenic element 82 gradually increases from the core to the edge, thereby forming an obvious core edge structure.

As described above, the zonal structure of pyrite in the pyrite-containing sample usually has a similar formation way with the uranium ore body in the reduced color sand body, for example, they are usually formed by an action of the same metallogenic fluid in the metallogenesis stage of the uranium ore body. However, no symbiotic relationship exists between the pyrite in the pyrite-containing sample and the uranium ore body in the reduced color sand body, the formation cause of the pyrite may not be the same as that of uranium. As a result, the relevant tests performed to the pyrite may not be used as a basis for judging that the reduced color sand body is undergone an action of the exudation fluid. For this reason, in the present embodiment, the symbiotic relationship between the pyrite and the uranium ore body is further determined, to ensure that the pyrite and the uranium ore body have a symbiotic relationship, and they are products formed by an action of the same metallogenic fluid in the metallogenesis stage of the ore body.

As described above, an image characterization work may be performed to the pyrite in the pyrite-containing sample, and the determination of whether a symbiotic relationship exists between the pyrite and the uranium ore body may also be completed by the image characterization work. Those skilled in the art may determine whether the pyrite is in a symbiotic relationship with the uranium ore body according to the relevant metallogeny theories in the art and the specific data obtained in the image characterization work.

Specific methods that may be used to determine whether the pyrite is in a symbiotic relationship with the uranium ore body are described below.

In some embodiments, it may be specifically determined whether the pyrite in the pyrite-containing sample is in a symbiotic relationship with the uranium in the reduced color sand body based on the distribution of the pyrite and the uranium in the pyrite-containing sample.

Figure 9A:
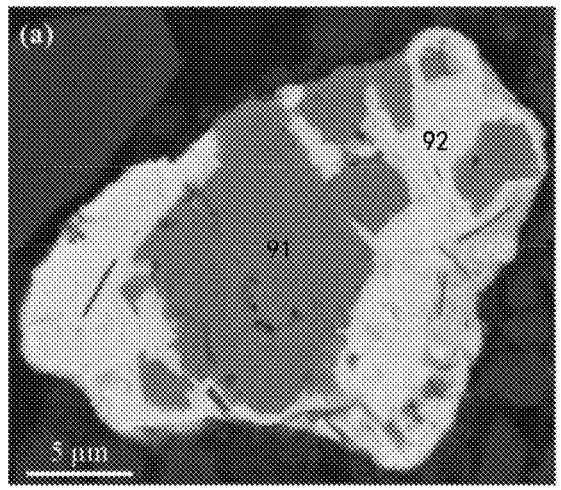
FIG. 9A and FIG. 9B show schematic diagrams of uranium distributed on a surface of pyrite in a pyrite-containing sample according to the embodiments of the present disclosure.
Figure 9B:
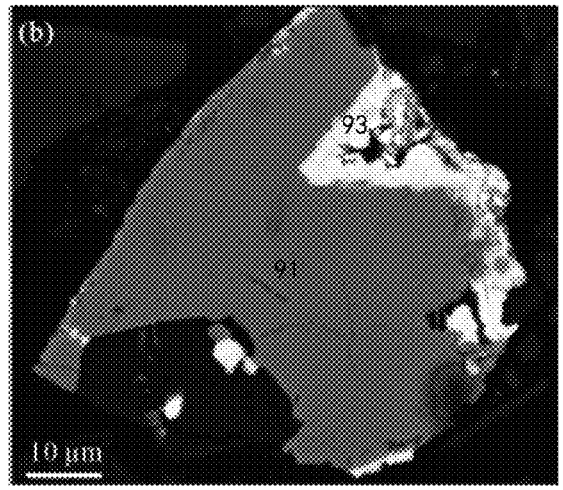

In some embodiments, referring to FIG. 9A and FIG. 9B, uranium minerals distributed on the surface of the pyrite may be observed in the energy spectrum scanning images, backscatter electron images etc. For example, in FIG. 9A, uranium mineral in the form of uranyl phosphate 92 is attached to the surface of pyrite 91, while in FIG. 9B, uranium mineral in the form of pitchblende 93 is attached to the surface of pyrite 91. The uranium distributed on the surface of pyrite in the form of pitchblende and/or uranyl phosphate may be used as a basis to determine that the pyrite is in a symbiotic relationship with the uranium ore body.

In some embodiments, it may be specifically determined whether the pyrite in the pyrite-containing sample is in a symbiotic relationship with the uranium ore body based on the attitude, spatial location, and formation sequence of the pyrite in the pyrite-containing sample.

Figure 10:
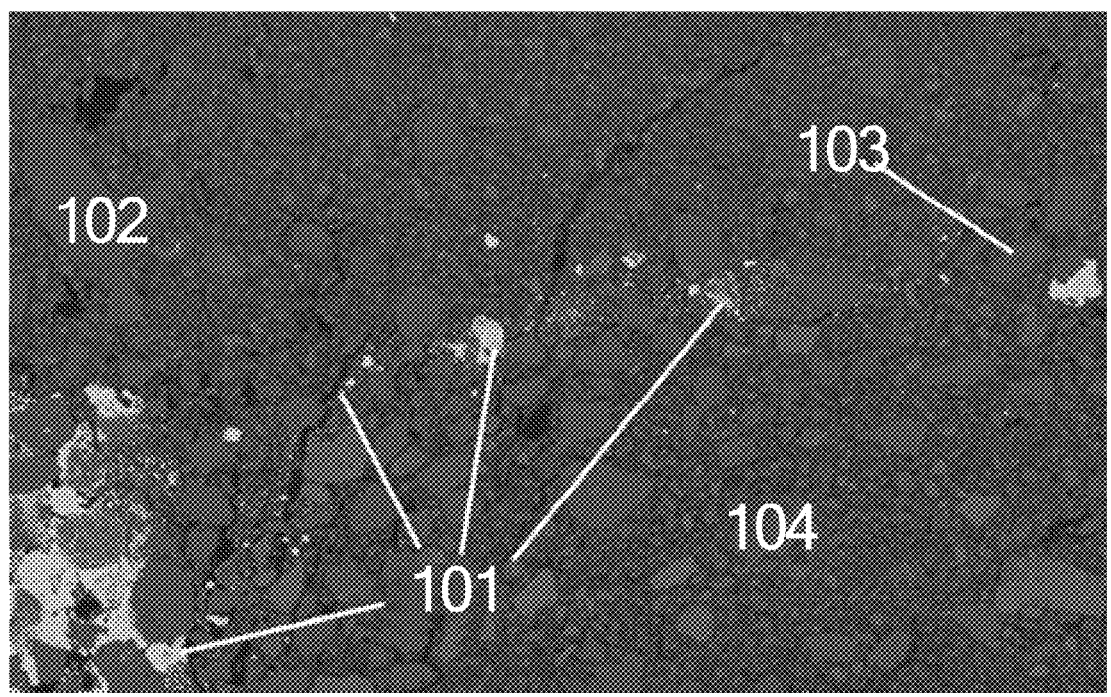
FIG. 10 shows a schematic diagram of pyrites having different attitudes in the pyrite-containing sample according to the embodiments of the present disclosure.

FIG. 10 shows a schematic diagram of different attitudes and distributions of a pyrite in a pyrite-containing sample. In the pyrite-containing sample, the attitude of pyrite 101 usually include veins, blocks, granules, etc., which are distributed in gray sandstones, and the gray sandstones also includes the clasts of various sandstones, such as quartz 102, plagioclase 103, potassium feldspar 104 and the like.

If the attitudes of pyrite 101 include veins, blocks and granules, and the pyrites in a shape of vein, block, and granule are distributed at locations where the particle sizes of the sandstones change in the pyrite-containing sample, this indicates that the pyrite is formed after the sandstone, which may be used as a basis for an existence of a symbiotic relationship between the pyrite and the uranium ore body. Further, if euhedral crystalline pyrites are distributed in the pyrite-containing sample, and the euhedral crystalline pyrites are formed after the zonal structure of the pyrite, this indicates that the pyrite in the pyrite-containing sample is formed in multiple stages, and the zonal structure of pyrite is more likely to be formed in the metallogenesis stage of the uranium ore body in the reduced color sand body, which may also be used as a basis for an existence of a symbiotic relationship between the pyrite and the uranium ore body.

In some embodiments, as described above, the determining an exudation uranium mineralization development location in the metallogenic depression region based on the region where an exudation fluid is developed, the fluid migration pathway, the metallogenic sand body distribution region and the uranium-producing reduced color sand body distribution region may specifically include: determining an overlapping region of the region where an exudation fluid is developed, the fluid migration pathway, the metallogenic sand body distribution region and the uranium-producing reduced color sand body distribution region; and determining the exudation uranium mineralization development location based on the overlapping region being located in the metallogenic depression region.

As shown in FIG. 2, the determined regions are not all on the same plane. When the overlapping region of these regions is determined, the determination is based on projections of these regions on the same plane, as shown in FIG. 3, and then the exudation uranium mineralization development location may be determined based on a projection of the overlapping region in the oxidized color formation.

In some embodiments, the determining the exudation uranium mineralization development location based on the overlapping region being located in the metallogenic depression region includes: determining the overlapping region and a region within a preset range around the overlapping region as the exudation uranium mineralization development location. It may be understood that a certain deviation may still exist in the overlapping region. Therefore, in the present embodiment, the overlapping region and a region within a preset range around the overlapping region are both determined as the exudation uranium mineralization development location to avoid errors and omissions. The preset range may be determined by those skilled in the art as required. As an example, the preset range may be 3-5 km.

Several methods that may be used to determine that a uranium ore body in the exudation uranium mineralization development location is an exudative sandstone uranium deposit are described below. The following methods may be used individually or in combination to determine whether an ore body is an exudative sandstone uranium deposit. It should be noted that, compared with the above step of determining whether the reduced color sand body is undergone an action of the exudation fluid, the present step will take a more macroscopic view to make a final determination whether a uranium ore body is an exudative sandstone uranium deposit.

In some embodiments, if the shape of the uranium ore body is plate-like and/or lenticular, the uranium ore body in the exudation uranium mineralization development location is determined as an exudative sandstone uranium deposit. Those skilled in the art may determine the shape of the uranium ore body by, for example, seismic profile analysis, inversion, etc.

In some embodiments, if in the uranium ore body an organic carbon content is greater than 0.27, and an acidolysis hydrocarbon content is greater than 460 $\mu L \cdot kg^{-1}$, the uranium ore body in the exudation uranium mineralization development location is determined as an exudative sandstone uranium deposit. Those skilled in the art may determine the organic carbon content and the acidolysis hydrocarbon content thereof by sampling and analyzing the uranium ore body.

In some embodiments, if a uranium in the uranium ore body is positively correlated with Co, Ni. Mo, and Zn, the uranium ore body in the exudation uranium mineralization development location is determined as an exudative sandstone uranium deposit.

In some embodiments, if concomitants of the uranium ore body include an asphalt and/or a pyrite with a low sulfur isotope ratio, the uranium ore body in the exudation uranium mineralization development location is determined as an exudative sandstone uranium deposit. As described above, the sulfur isotope value in the pyrite that is undergone an action of the exudation fluid gradually decreases from the core to the edge, resulting in a low sulfur isotope ratio of the pyrite. Therefore, if a pyrite with a low sulfur isotope ratio is found, it is determined that the uranium ore body in the exudation uranium mineralization development location is determined as an exudative sandstone uranium deposit.

In some embodiments, if a ratio of a total thickness of the reduced color sand body in the exudation uranium mineralization development location to a total thickness of a sand body is 25%-75%, the uranium ore body in the exudation uranium mineralization development location is determined as an exudative sandstone uranium deposit. Here, the total thickness of the sand body refers to a total thickness of all sand bodies, including the reduced color sand body. The ratio of the total thickness of the reduced color sand body to the total thickness of the sand body may also be called a lime sand ratio. If the lime sand ratio is between 25% and 75%, it may be determined that the uranium ore body in the exudation uranium mineralization development location an exudative sandstone uranium deposit.

One or more embodiments described above will be described and supplemented in more detail below by taking the Hadatu uranium deposit in the Erlian Basin as an example.

First, the Qiharigetu depression in the Erlian Basin is identified as a metallogenic depression region.

Specifically, according to the geological data survey, the Qiharigetu depression in the Erlian has a basement buried depth of 2000 m and an area of 1800 km$^2$. The overlying strata has a binary structure. The lower horizon of Arshan Formation and Tengger Formation is a set of gray and gray green formations producing oil, i.e., a reduced color formation. The upper section of the overlying Saihan Formation is a set of oxidized red variegated fluvial facies sedimentary formation, i.e., an oxidized color formation. Therefore, Qiharigetu is determined as a metallogenic depression.

Next, a region where a hydrocarbon source rock is located in the lower Tengger Formation is determined as the uranium source region.

Specifically, based on data analysis, the uranium content of the reduced color formation in the lower Tengger Formation of the Qiharigetu depression is $7.5\times10^{-6}$-$12.6\times10^{-6}$, and the uranium content in the dolomite of the hydrocarbon source rock reaches $40\times10^{-6}$ to $60\times10^{-6}$. Therefore, ta region where the hydrocarbon source rock of the Tengger Formation is located in the reduced color formation is determined as the uranium source region.

Next, a region where an exudation fluid is developed in the Tengger Formation is determined.

Specifically, the hydrocarbon source rock of the Tengger Formation in the Qiharigetu depression has a high organic matter abundance (TOC=1.40%-3.48%, average 2.69%), good parent material types (mainly type II 1, some types I and II 2), a high hydrocarbon generation potential (S1+S2=2.49-15.56 mg/g, average 12.42 mg/g), and organic matters mainly in the low maturity-high maturity stage (Ro=0.5%-1.3%), which is a rich organic fluid matrix in this region. An analysis of a liquid rich brine inclusion inside the quartz grains in the ore shows that an inclusion homogenization temperature is (65-165)° C., and the salinity is (6.0-8.0) (wt % NaCl). The combination of the two shows that an exudation fluid is developed in the Tengger Formation of the Qiharigetu depression.

Next, determine the fluid migration pathway is determined.

The upper section of the Saihan Formation and the Tengger Formation in the Qiharigetu depression are in a high angular unconformity contact relationship. A paleo channel developed in the upper section of the Saihan Formation cuts down into the Tengger Formation, and two sets of fracture are developed in the depression, one set is distributed in an NE direction, and one set is distributed in a near SN direction. The above fractures, cut-down paleo channel, and angular unconformity become a fluid migration pathway for an upward migration of an exudation fluid produced in the deep Tengger Formation.

Next, a metallogenic sand body distribution region is determined.

In the upper section of Saihan Formation of the red variegated layer in Qiharigetu depression, a paleo channel having a width of 10-20 km and a length of 60 km is generally developed from south to north, and a single-layer sand body has a thickness of 40-80 m. Therefore, the paleo channel developed in the upper section of Saihan Formation is determined as a metallogenic sand body distribution region favorable for exudation metallogenesis.

Next, a uranium-producing reduced color sand body distribution region formed by an action of the exudation fluid is determined in the metallogenic sand body distribution region.

For the paleo channel developed in the upper section of Saihan Formation in the Qiharigetu depression, a channel intersection is developed in the north and west of the depression, and gray sand bodies are developed in locations where the channel becomes wider and slower in the east of the central portion of the depression. In the gray sand bodies, spotty ferritization remains are seen in the mud gravel enclosed by the gray sand bodies and parts of the gray sand bodies. Dynamic organic matter and oil immersed sandstone may be seen in the sand bodies. The Co content in the sand bodies reaches $23.42\times10^{-6}$, which is 3.5 times of a background value. The Ni content reaches $26.60\times10^{-6}$, which is 3.8 times of a background value. The Zn content reaches $68.69\times10^{-6}$, which is 3.3 times of a background value. The uranium content reaches $12.78\times10^{-6}$. Therefore, this location is determined as a uranium-producing reduced color sand body distribution region formed by an action of the exudation fluid.

Next, an exudation uranium mineralization development location is determined based on the region determined above.

An overlapping analysis is performed to the Qiharigetu depression (the metallogenic depression region), the hydrocarbon source rock distribution region in the Tengger Formation (the region where an exudation fluid is developed), the paleo channel in the upper section of the Saihan Formation (the metallogenic sand body distribution region and the uranium-producing reduced color sand body distribution region) and the fracture (the fluid migration pathway). The overlapping region of the four elements is extended outward by 3 km, and the obtained region is a favorable location for the exudation uranium mineralization development. Three exudation uranium metallogenic development locations of HDT, QLG, and QH are determined in the Qiharigetu depression. At present, the three confirmed favorable regions for exudation metallogenesis have been identified as a super huge uranium deposit, a uranium ore producing region and a prospecting target region.

Next, a uranium ore body in the exudation uranium mineralization development location is determined as the exudative sandstone uranium deposit.

By statistically analyzing the total thickness of sand body and the thickness of gray sand body in the red variegated layer of Hadatu uranium deposit, it is concluded that the lime sand ratio at the ore body is 25%-75%; the ore body is suspended in the red variegated glutenite in a plate form; the organic carbon content in the ore is larger than 0.27%, the acidolysis hydrocarbon content is larger than 460 μL· kg$^{-1}$, and uranium is obviously positively correlated with deep source basic elements Co, Ni and sulfophile elements Mo, Zn. It is found by scanning electron microscope that uranium mineral (mainly pitchblende) is co-produced with ground asphalt and pyrite in the Hadatu uranium deposit. Therefore, the Hadatu uranium deposit is determined as an exudative sandstone uranium deposit.

The present disclosure has been described in detail above in combination with the accompanying drawings and embodiments, but the present disclosure is not limited to the above embodiments. Within the scope of knowledge possessed by those skilled in the art, various modifications may be made without departing from the objectives of the present disclosure. The contents not described in detail in the present disclosure may be performed by the prior art.

What is claimed is:

1. A method for identifying an exudative sandstone uranium deposit, comprising:
   determining a metallogenic depression region in a sedimentary basin, wherein a region in the sedimentary basin where an oxidized color formation is developed and a reduced color formation is developed below the oxidized color formation is determined as the metallogenic depression region;
   determining a uranium source region in the metallogenic depression region, wherein a region having a uranium content greater than a preset value in the reduced color formation is determined as the uranium source region, wherein the uranium content in the reduced color formation is determined by performing sampling and analysis as well as drilling core analysis to a leakage profile rock of the reduced color formation, or performing radioactive logging to the reduced color formation;
   determining a region where an exudation fluid is developed in the metallogenic depression region;
   determining a fluid migration pathway in the metallogenic depression region, wherein a horizon and fault interpretation to boreholes and seismic profile is performed in the metallogenic depression region to determine the fracture structure in the metallogenic depression region, and the fracture structure connecting the reduced color formation with the oxidized color formation is determined as the fluid migration pathway;
   determining a metallogenic sand body distribution region in the oxidized color formation, wherein the metallogenic sand body distribution region is determined by method for locating a sand body;
   determining a uranium-producing reduced color sand body distribution region formed by an action of the exudation fluid in the metallogenic sand body distribution region, wherein the uranium-producing reduced color sand body distribution region is determined by performing sampling and analysis;
   determining an exudation uranium mineralization development location in the metallogenic depression region, wherein the exudation uranium mineralization development location is determined in the metallogenic depression region based on the region where the exudation fluid is developed, the fluid migration pathway, the metallogenic sand body distribution region and the uranium-producing reduced color sand body distribution region;
   determining whether a uranium ore body in the exudation uranium mineralization development location is the exudative sandstone uranium deposit, wherein it is determined whether the uranium ore body in the exudation uranium mineralization development location is an exudative sandstone uranium deposit based on at least one of a shape of the uranium ore body, a symbiont of the uranium ore body, a thickness of the reduced color sand body, and an element component of the uranium ore body in the exudation uranium mineralization development location; and
   if it is determined that the uranium ore body in the exudation uranium mineralization development location is the exudative sandstone uranium deposit, comprehensively evaluating a distribution range and a uranium content of the uranium ore body in the exudation uranium mineralization development location based on a principle of an exudation uranium metallogenesis, so as to avoid occurrence of ore leakage and ore missing,
   wherein the determining a region where an exudation fluid is developed in the metallogenic depression region comprises:
   determining a composition, a temperature and a salinity of a fluid inclusion in the reduced color formation; and
   determining that the exudation fluid is developed in the region where the reduced color formation is located if an organic matter is developed in the fluid inclusion, and the temperature is greater than 90° C. and the salinity is greater than 4%,
   wherein the composition of the fluid inclusion is analyzed using a laser Raman spectrometer, an infrared spectrometer, a gas chromatograph, or an isotope mass spectrometer, and the temperature and the salinity of the fluid inclusion is measured using a microscopic cooling and heating table.

2. The method according to claim 1, wherein the determining a metallogenic depression region in a sedimentary basin comprises:
   determining a depression region in the sedimentary basin; and
   determining a region in the depression region where the oxidized color formation is developed and the reduced color formation is developed below the oxidized color formation as the metallogenic depression region, wherein the reduced color formation comprises a hydrocarbon source rock and/or a gray mudstone having a thickness greater than a second preset value.

3. The method according to claim 2, wherein the determining a depression region in the sedimentary basin comprises:
   determining a region in the sedimentary basin where a depression basement buried depth is greater than 1500 m and an area is greater than 800 km$^2$ is determined as the depression region.

4. The method according to claim 1, wherein the determining a region where an exudation fluid is developed in the metallogenic depression region comprises:
   determining a content of uranium and sulfophile elements in a reduced color sand body in the oxidized color formation;
   determining a content of uranium and sulfophile elements in the oxidized color sand body distributed at a same time and space as the reduced color sand body; and
   determining that the exudation fluid is developed in the region where the reduced color sand body is located, if the content of uranium and sulfophile elements in the reduced color sand body is greater than the content of uranium and sulfophile elements in the oxidized color sand body and exceeds a third preset value.

5. The method according to claim 1, wherein the determining a fluid migration pathway in the metallogenic depression region comprises:
determining a fracture structure in the metallogenic depression region connecting the reduced color formation with the oxidized color formation as the fluid migration pathway.

6. The method according to claim 1, wherein the determining a fluid migration pathway in the metallogenic depression region comprises:
determining a region where a riverway is developed in the oxidized color formation and where the riverway is cut down to the reduced color formation as the fluid migration pathway.

7. The method according to claim 1, wherein the determining a fluid migration pathway in the metallogenic depression region comprises:
determining a region exhibiting an unconformity of a contact relationship between the oxidized color formation and the reduced color formation as the fluid migration pathway.

8. The method according to claim 5, wherein the determining a fluid migration pathway in the metallogenic depression region comprises:
determining a permeable sand body and an unconformity plane that are related to the fracture structure as the fluid migration pathway.

9. The method according to claim 1, wherein the determining a metallogenic sand body distribution region in the oxidized color formation comprises:
determining a fluvial facies region in the oxidized color formation; and
determining a region in the fluvial facies region where a sand body thickness is greater than 20 m and an area is greater than 30 km² as the metallogenic sand body distribution region.

10. The method according to claim 1, wherein the determining a uranium-producing reduced color sand body distribution region formed by an action of the exudation fluid in the metallogenic sand body distribution region comprises:
sampling and analyzing the reduced color sand body in the metallogenic sand body distribution region, so as to determine whether the reduced color sand body is formed by an action of the exudation fluid and whether the reduced color sand body is a uranium-producing reduced color sand body.

11. The method according to claim 10, wherein the sampling and analyzing the reduced color sand body comprises:
sampling the reduced color sand body, and analyzing sandstone rock mineral characteristics of the reduced color sand body; and
determining that the reduced color sand body is formed by an action of the exudation fluid, if the sandstone rock mineral characteristics in the reduced color sand body comprise at least one of:
a limonitization spot existing in the reduced color sand body, a limonitization spot existing in a boulder clay enclosed by the reduced color sand body, and the reduced color sand body being embedded in the oxidized color sand body along a fracture.

12. The method according to claim 10, wherein the sampling and analyzing the reduced color sand body comprises:
sampling the reduced color sand body, and analyzing an element enrichment in the reduced color sand body; and
determining that the reduced color sand body is formed by an action of the exudation fluid, if an enrichment of Co, Ni, Zn, and Mo in the reduced color sand body is higher than that of a primary sand body and exceeds a fourth preset value.

13. The method according to claim 10, wherein the sampling and analyzing the reduced color sand body comprises:
sampling the reduced color sand body, and determining a source of the organic matter in the reduced color sand body; and
determining that the reduced color sand body is formed by an action of the exudation fluid, if an organic matter originating from the reduced color formation exists in the reduced color sand body.

14. The method according to claim 10, wherein the sampling and analyzing the reduced color sand body comprises:
sampling the reduced color sand body, and analyzing a uranium content in the reduced color sand body; and
determining the reduced color sand body as the uranium-producing reduced color sand body, if the uranium content in the reduced color sand body is greater than a fifth preset value.

15. The method according to claim 1, wherein the determining an exudation uranium mineralization development location in the metallogenic depression region comprises:
determining an overlapping region between the region where an exudation fluid is developed in the uranium source region, the fluid migration pathway, the metallogenic sand body distribution region and the uranium-producing reduced color sand body distribution region; and
determining the exudation uranium mineralization development location based on the overlapping region being located in the metallogenic depression region.

16. The method according to claim 15, wherein the determining the exudation uranium mineralization development location based on the overlapping region being located in the metallogenic depression region comprises:
determining the overlapping region and a region within a preset range around the overlapping region as the exudation uranium mineralization development location.

17. The method according to claim 1, wherein if the shape of the uranium ore body is plate-like and/or lenticular, the uranium ore body in the exudation uranium mineralization development location is determined as an exudative sandstone uranium deposit.

18. The method according to claim 1, wherein if in the uranium ore body an organic carbon content is greater than 0.27 and an acidolysis hydrocarbon content is greater than 460 $\mu L \cdot kg^{-1}$, the uranium ore body in the exudation uranium mineralization development location is determined as an exudative sandstone uranium deposit.

19. The method according to claim 1, wherein if a uranium in the uranium ore body is positively correlated with Co, Ni, Mo, and Zn, the uranium ore body in the exudation uranium mineralization development location is determined as an exudative sandstone uranium deposit;
wherein if concomitants of the uranium ore body comprise an asphalt and/or a pyrite with a low sulfur isotope ratio, the uranium ore body in the exudation uranium mineralization development location is determined as an exudative sandstone uranium deposit; and
wherein if a ratio of a total thickness of the reduced color sand body in the exudation uranium mineralization development location to a total thickness of a sand body is 25%-75%, the uranium ore body in the exudation uranium mineralization development location is determined as an exudative sandstone uranium deposit.

* * * * *